(12) United States Patent
Zhang et al.

(10) Patent No.: US 10,743,879 B2
(45) Date of Patent: Aug. 18, 2020

(54) ELECTRIC SURGICAL STAPLER

(71) Applicant: SUZHOU INTOCARE MEDICAL TECHNOLOGY CO., LTD., Suzhou (CN)

(72) Inventors: Hui Zhang, Suzhou (CN); Yunfeng Du, Suzhou (CN); Dianchen Liu, Suzhou (CN); Aiyu Huang, Suzhou (CN)

(73) Assignee: SUZHOU INTOCARE MEDICAL TECHNOLOGY CO., LTD., Suzhou (CN)

( * ) Notice: Subject to any disclaimer, the term of this patent is extended or adjusted under 35 U.S.C. 154(b) by 343 days.

(21) Appl. No.: 15/567,153

(22) PCT Filed: Jul. 29, 2016

(86) PCT No.: PCT/CN2016/092393
§ 371 (c)(1),
(2) Date: Oct. 17, 2017

(87) PCT Pub. No.: WO2017/107488
PCT Pub. Date: Jun. 29, 2017

(65) Prior Publication Data
US 2018/0098768 A1 Apr. 12, 2018

(30) Foreign Application Priority Data
Dec. 22, 2015 (CN) .......................... 2015 1 0974054

(51) Int. Cl.
*A61B 17/115* (2006.01)
*A61B 17/072* (2006.01)
(Continued)

(52) U.S. Cl.
CPC ........ *A61B 17/1155* (2013.01); *A61B 17/072* (2013.01); *A61B 17/1114* (2013.01);
(Continued)

(58) Field of Classification Search
CPC ... A61B 17/105; A61B 17/072; A61B 17/068; A61B 17/115
(Continued)

(56) References Cited

U.S. PATENT DOCUMENTS

2006/0289600 A1 12/2006 Wales et al.
2007/0270784 A1* 11/2007 Smith ................. A61B 17/1114
606/1
(Continued)

FOREIGN PATENT DOCUMENTS

CN 101467907 A 7/2009
CN 102247182 A 11/2011
(Continued)

OTHER PUBLICATIONS

European Search Report for Application No. 16877300.0 dated Jul. 10, 2019, 8 pages.
(Continued)

*Primary Examiner* — Nathaniel C Chukwurah
(74) *Attorney, Agent, or Firm* — Seyfarth Shaw LLP

(57) ABSTRACT

An electric surgical stapler including a handle and a working head. The handle has a handle body, a driving motor, and a control unit for controlling the driving motor to operate. The working head includes an anvil, a cartridge, a closing mechanism, a firing mechanism, a housing for accommodating the closing mechanism and the firing mechanism, a closing limit switch configured to transmit information of a closing stroke of the closing mechanism to the control unit, and a pressure sensor configured to transmit a pressure value applied to a squeezed tissue during closing to the control unit. The control unit is configured to transmit an instruction of controlling the driving motor to drive movement of the
(Continued)

firing mechanism, when the closing limit switch is triggered and the pressure value transmitted by the pressure sensor meets a preset standard.

10 Claims, 3 Drawing Sheets

(51) Int. Cl.
    *A61B 17/11*     (2006.01)
    *A61B 17/00*     (2006.01)
    *A61B 90/00*     (2016.01)
(52) U.S. Cl.
    CPC ........... *A61B 2017/00017* (2013.01); *A61B 2017/00022* (2013.01); *A61B 2017/0046* (2013.01); *A61B 2017/00115* (2013.01); *A61B 2017/00389* (2013.01); *A61B 2017/00398* (2013.01); *A61B 2017/00734* (2013.01); *A61B 2090/065* (2016.02)
(58) Field of Classification Search
    USPC ........................................... 227/175.1–180.1
    See application file for complete search history.

(56)         References Cited

U.S. PATENT DOCUMENTS

| 2011/0174861 | A1 | 7/2011 | Shelton, IV et al. |
| 2013/0193188 | A1 | 8/2013 | Shelton, IV et al. |
| 2013/0200131 | A1 | 8/2013 | Racenet et al. |
| 2014/0305987 | A1 | 10/2014 | Parihar et al. |
| 2014/0305991 | A1 | 10/2014 | Parihar et al. |
| 2014/0305992 | A1* | 10/2014 | Kimsey ............... A61B 17/068 227/176.1 |
| 2016/0249927 | A1 | 9/2016 | Beckman et al. |

FOREIGN PATENT DOCUMENTS

| CN | 103110439 | A | 5/2013 |
| CN | 103405254 | A | 11/2013 |
| CN | 103405257 | A | 11/2013 |
| CN | 103784175 | A | 5/2014 |
| CN | 104367361 | A | 2/2015 |
| CN | 105395232 | A | 3/2016 |
| CN | 105411641 | A | 3/2016 |
| CN | 105411642 | A | 3/2016 |
| CN | 105596046 | A | 5/2016 |
| WO | 2016137810 | A1 | 9/2016 |

OTHER PUBLICATIONS

Second Office Action for Chinese Application No. 201510974054.2 dated Jan. 24, 2018, 7 pages.
Third Office Action for Chinese Application No. 201510974054.2 dated Jul. 17, 2018, 3 pages.
Ohinese Office Action for Chinese Application No. 201510974054.2 dated May 2, 2017, 5 pages.
Written Opinion for International Application No. PCT/CN2016/092393 dated Oct. 27, 2016, 5 pages.
International Search Report for International Application No. PCT/CN2016/092393 dated Oct. 26, 2016, 6 pages.

* cited by examiner

ELECTRIC SURGICAL STAPLER

CROSS REFERENCE TO RELATED APPLICATIONS

This is a National Stage application of PCT/CN2016/092393, filed Jul. 29, 2016, and claims priority to Chinese Patent Application Serial No. CN 201510974054.2, filed Dec. 22, 2015, the disclosures of which are incorporated herein by reference.

TECHNICAL FIELD

The present disclosure relates to the technical field of medical equipment, and more particularly, to an electric surgical stapler.

BACKGROUND

The surgical stapler is a common medical device when performing a surgical procedure on tissues of the digestive tract. During the surgical treatment, the surgical stapler is often use in tissue cutting and stapling. The surgical stapler may perform closing, stapling or cutting operations on the physiological tissue manually or electrically.

The manual operation implements the closing action between the anvil and the cartridge, and the firing action on the tissue to be stapled in a purely mechanical way. The process of the firing needs huge firing force to complete the cutting and closing, with high requirement for the user. It is easy to cause the mechanical firing to fail once the skills and the strength of force and not mastered properly. The closing effect of the tissue will be affected by inadequate firing force, to cause inadequate cutting and closing, resulting in failure of surgery, and extremely high risk. There is no risk of inadequate firing force for an electric surgical stapler as long as it has adequate power.

With manual surgical staplers, however, a surgeon needs to determine an appropriate tissue compression (from 1.5 mm to 2.5 mm within a green zone range) according to the experience completely, rather than obtaining exact tissue compression corresponding to tissue characteristics of different patients. The error caused by determining the compression thickness of the tissue based on experiences may lead to large discreteness of postoperative effects of different patients, which not only affects the efficiency of the surgery, but also causes inconsistent staple formations, two-step staple formation, and other phenomena.

SUMMARY

Based on the above, an objective of the present disclosure is to provide an electric surgical stapler, which can effectively ensure best tissue compression pressure and the stable stapling effect.

According to an aspect of the present disclosure, an electric surgical stapler is provided, including: a handle, including a handle body, a driving motor and a control unit for controlling the driving motor to operate; a working head, including an anvil, a cartridge, a closing mechanism, a firing mechanism, a housing for accommodating the closing mechanism and the firing mechanism, a closing limit switch configured to transmit information of a closing stroke of the closing mechanism to the control unit, and a pressure sensor configured to transmit a pressure value applied to a squeezed tissue during closing to the control unit; wherein the control unit is configured to transmit an instruction of controlling the driving motor to drive movement of the firing mechanism, when the closing limit switch is triggered and the pressure value transmitted by the pressure sensor meets a preset standard.

The above electric stapler uses the closing limit switch to detect whether the closing stroke has reached the preset range and detects the pressure from the squeezed tissue with the pressure sensor. The control board only issues a firing instruction when both the closing stroke and the pressure coincide respectively with the preset range. In this way, there is no excessive squeezing or inadequate squeezing, which ensures that the tissue is squeezed adequately regardless of the thickness, and can ensure stable effect of the staple formation.

In one embodiment, the closing mechanism includes a first linear motion component configured to drive the anvil to move or drive the cartridge to move, and the firing mechanism includes a second linear motion component configured to push a staple ejecting assembly in the cartridge to move.

In one embodiment, the closing mechanism includes a closing main shaft driven by an output shaft of the driving motor to rotate, the first linear motion component is configured to be driven by the closing main shaft and drive the anvil to move, the firing mechanism includes a firing main shaft driven by the output shaft of the driving motor to rotate, the second linear motion component is configured to be driven by the firing main shaft and act on the staple ejecting plate in the cartridge, and the pressure sensor is arranged on the anvil, the cartridge or in a motion path of the first linear motion component.

In one embodiment, the electric surgical stapler further includes a firing safety switch having a first operating position and a second operating position, the firing safety switch allows the output shaft to transmit torque to the closing main shaft when the firing safety switch is at the first operating position, and the firing safety switch allows the output shaft to transmit torque to the firing main shaft when the firing safety switch is at the second operating position.

In one embodiment, a closing switch and an opening switch connected to the control unit are arranged outside the handle body, the control unit is configured to transmit an instruction of controlling the driving motor to drive the closing main shaft to move when detecting that the closing switch is triggered and the firing safety switch is at the first operating position, and the control unit is further configured to transmit an instruction of controlling the driving motor to drive the firing main shaft to move when detecting that the closing switch is triggered, the firing safety switch is at the second operating position, and the closing limit switch is in a triggered state.

In one embodiment, the electric surgical stapler further includes a firing limit switch configured to detect and transmit position information of the second linear motion component to the control unit, and the control unit is further configured to stop the operation of the driving motor when the second linear motion component comes within a preset position range and triggers the firing limit switch.

In one embodiment, the closing limit switch is an optoelectronic switch, a micro switch or a proximity switch.

In one embodiment, a manual adjustment knob is arranged on an outer wall of the handle body, and the manual adjustment knob is configured to drive the output shaft to rotate when the manual adjustment knob rotates.

In one embodiment, the housing is removably connected to the handle body, the working head and the driving device are assembled together when the housing is connected to the handle body, and the working head is separated from the driving device when the housing is removed from the handle body.

In one embodiment, a data interface for being connected to the pressure sensor, the closing limit switch and the firing limit switch is arranged inside the handle body, and the data interface is connected to the control unit.

In one embodiment, a release button is arranged outside the handle body, and the release button has a locking position for locking the housing and a release position for unlocking the housing.

In one embodiment, a window for observing the position of the closing main shaft is arranged on the housing.

In one embodiment, the electric surgical stapler further includes a replaceable battery pack configured to be connected to the handle body and supply power to the driving motor.

In one embodiment, a battery volume indicator connected to the control unit is arranged on the handle body.

DETAILED DESCRIPTION

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

The preferred embodiments of the electric surgical stapler will be described taken in conjunction with the accompanying drawings.

Figure 1:
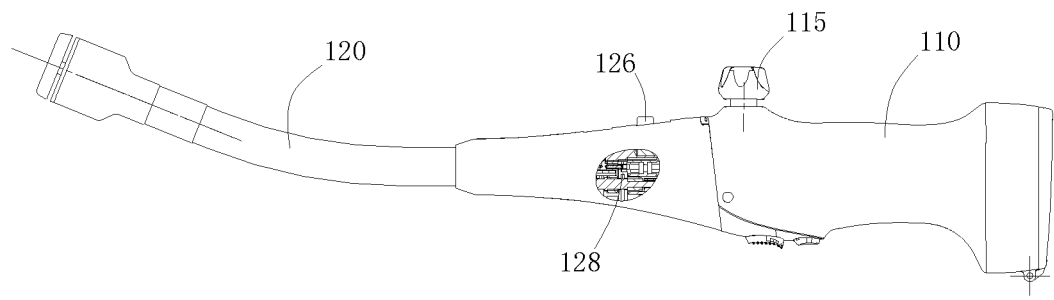
FIG. 1 is a schematic diagram illustrating an electric surgical stapler according to Example One of the present disclosure.

With reference to FIG. 1, an electric surgical stapler is provided, including a handle 110 and a replaceable working head 120.

Figure 2:
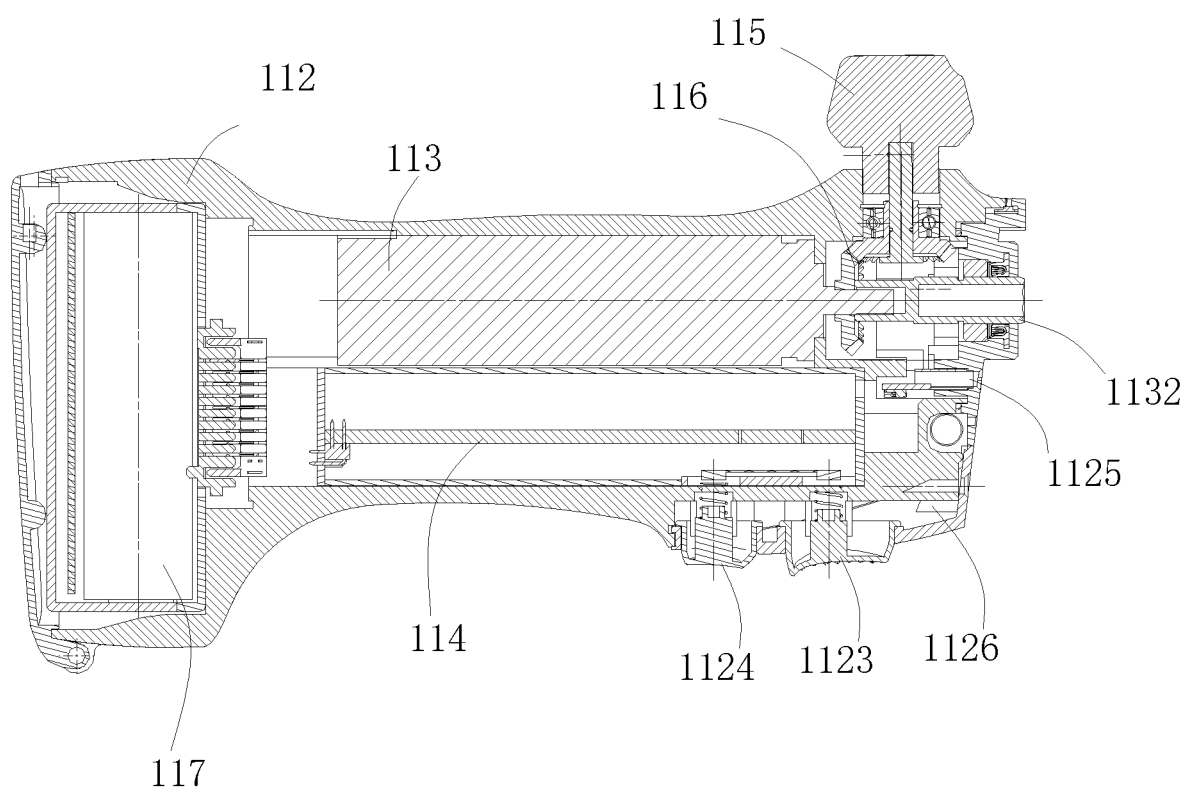
FIG. 2 is a schematic diagram illustrating a handle of the electric surgical stapler according to Example One of the present disclosure.

With reference to FIG. 2, the handle 110 is a driving device for driving the working head 120 to operate, including a hollow handle body 112, a driving motor 113 with an output shaft 1132, and a control unit 114, and the driving motor 113 and the control unit 114 are arranged inside the handle body 112.

The outer wall of the handle body 112 is provided with an adjustment knob 115. The adjustment knob 115 is connected to the output shaft 1132 through a bevel gear system 116. When the driving motor 113 stops, the user may turn the adjustment knob 115, and the bevel gear system 116 may drive the output shaft 1132 to rotate, to achieve manual adjustment. In this way, when there is a failure in the electric system, the manual mode can be enabled to use the adjustment knob 115 to open the jaw of the working head 120 or finish firing.

In this example, the working head 120 is a circular stapling head, including an anvil 121, cartridge 122, a closing mechanism, a firing mechanism, and a housing 125 accommodating the closing mechanism and the firing mechanism.

The closing mechanism includes a closing main shaft 1232 and a closing transmission mechanism. The closing main shaft 1232 is driven by a driving motor 113 to rotate. The closing transmission mechanism is connected to the anvil 121. When the closing main shaft 1232 rotates, a first linear motion component in the closing transmission mechanism drives the anvil 121 to move in a straight line. The first linear motion component includes a first sliding block 1234 and a first push rod 1235 driven by the first sliding block 1234. The first sliding block 1234 is connected to the closing main shaft 1232 in a helical transmission form, but the rotation of the first sliding block 1234 is limited. When the closing main shaft 1232 rotates, the first sliding block 1234 is able to move in a straight line, and drive the movement of the anvil 121 through the first push rod 1235.

The firing mechanism includes a firing main shaft 1242 and a firing transmission mechanism. The firing main shaft 1242 is driven by the driving motor 113 to rotate. The firing transmission mechanism is connected to a staple ejecting plate. When the firing main shaft 1242 rotates, a second linear motion component in the firing transmission mechanism causes the staple ejecting plate to perform firing actions. In this example, the second linear motion component is similar to the first linear motion component in the closing transmission mechanism. The second linear motion component includes a second sliding block 1244 and a second push rod 1245 driven by the second sliding block 1244. When the firing main shaft 1242 rotates, the second sliding block 1244 is able to move in a straight line, and drive the movement of the staple ejecting assemblies in the cartridge 122 through the second push rod 1435.

The working head 120 further includes a firing safety switch 126 mounted on the housing 125. The firing safety switch 126 has a first operating position and a second operating position. The firing safety switch 126 allows the output shaft 1132 to transmit torque to the closing main shaft 1232 when the firing safety switch 126 is at the first operating position, and the first operating position is defined as a closing position. The firing safety switch 126 allows the output shaft 1132 to transmit torque to the firing main shaft 1242 when the firing safety switch 126 is at the second operating position, and the second operating position is defined as a firing position.

The firing safety switch 126 fits a switching transmission mechanism in the housing 125. The switching transmission mechanism includes an input shaft 1271, a switching shaft 1272, a switching driving lever 1273, a first switching ring 1274, a first guide block 1275, a second switching ring 1276 and a second guide block 1277 matching and connected to the output shaft 1132.

The input shaft 1271 transmits power to the switching shaft 1272 through a gear mechanism. The first guide block 1275 is fastened to the input shaft 1271, the first switching ring 1274 is able to drive the closing main shaft 1232 to rotate, and be driven by the switching driving lever 1273 to be engaged with or disengaged from the first guide block 1275. The second guide block 1277 is fastened to the firing main shaft 1242, the second switching ring 1276 is able to drive the firing main shaft 1242 to rotate, and be driven by the switching driving lever 1273 to be engaged with or disengaged from the second guide block 1277.

The firing safety switch 126 may be operated to drive the switching driving lever 1273, so that the first switching ring 1274 is engaged with the first guide block 1275 while the second switching ring 1276 is disengaged from the second guide block 1277, or the first switching ring 1274 is disengaged from the first guide block 1275 while the second switching ring 1276 is engaged with the second guide block 1277. In this way, the switching of the power transmission can be achieved by operating the firing safety switch 126.

The switching transmission mechanism may be implemented in other forms. For example, an intermediate shaft and a switching member matching and connected to the output shaft 1132 may be provided. The switching member may make an axially upward movement on the intermediate shaft, the switching member may connect the intermediate shaft to the closing main shaft 1232 at the first operating position, and the switching member may connect the intermediate shaft to the firing main shaft 1242 at the second operating position.

The handle 110 is only internally provided one driving motor 113 and one output shaft, and can switch power transmission by the firing safety switch 126. There may also be two driving motors 113, that is one driving motor is adapted to drive the closing main shaft 1232 alone, and the other driving motor is adapted to drive the firing main shaft alone.

Further, the firing safety switch 126 is mounted on the housing 125. The firing safety switch 126 may also be arranged on the handle body 112, that is, the switching mechanism for power transmission may be arranged within the handle 110.

Figure 3:
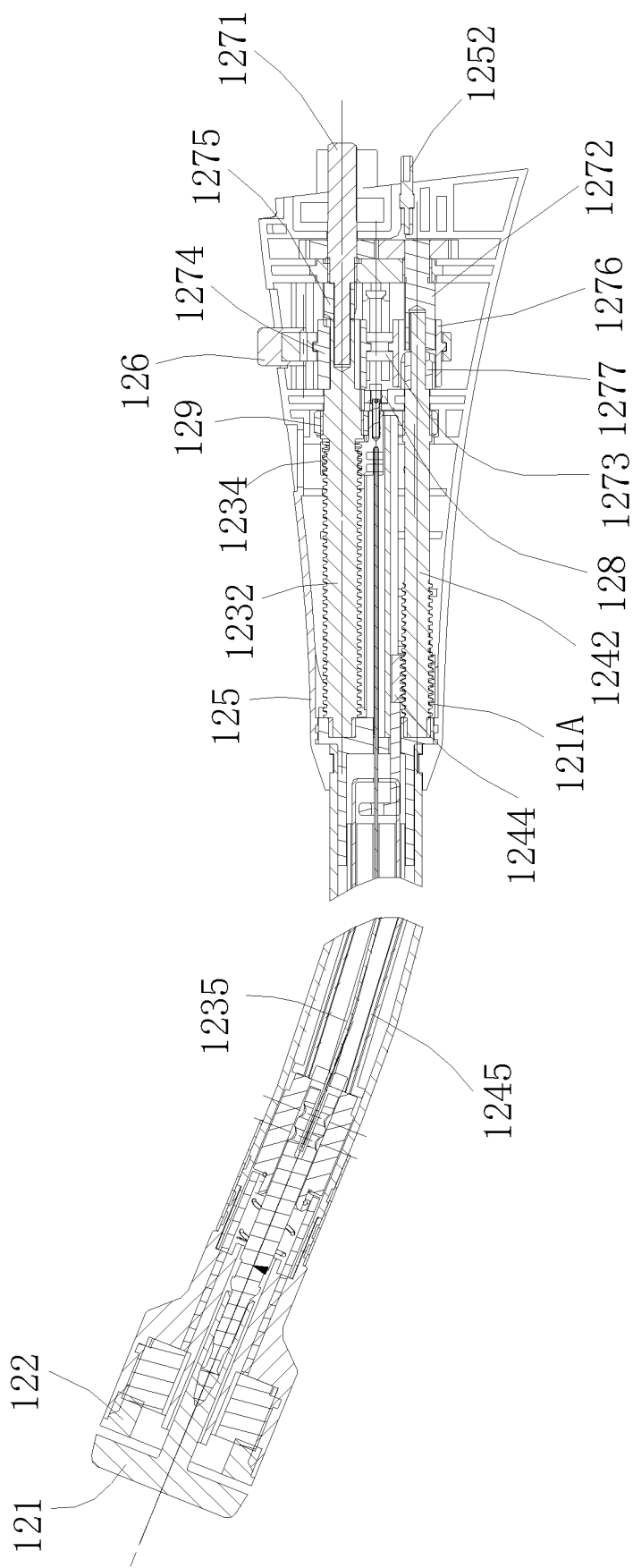
FIG. 3 is a schematic diagram illustrating a circular stapling head in the electric surgical stapler according to Example One of the present disclosure.

With reference to FIG. 3, the working head 120 also includes a closing limit switch 128 and a pressure sensor 129.

The closing limit switch 128 is configured to detect the closing stroke of the closing mechanism, and transmit information of the closing stroke to the control unit 114. The closing limit switch 128 may be an optoelectronic switch, a micro switch or a proximity switch.

The closing limit switch 128 is mounted on the housing 125. When the first linear motion component in the closing mechanism moves to a closing position within a preset range, the closing limit switch 128 may be triggered to transmit a signal to the control unit 114, indicating that the closing stroke comes within a preset range.

The pressure sensor 129 is configured to detect the value of the closing pressure applied on the tissues between the anvil 121 and the cartridge 122 when the closing mechanism performs a closing action, and transmit the value of the closing pressure to the control unit 114. The pressure sensor 129 may be arranged on the motion path of the first linear motion component, or may be arranged on the anvil 22 or the cartridge 122.

When the driving motor 120 is activated, and the firing safety switch 126 is at the closing position, the closing mechanism operates, the anvil 121 is gradually closed against the cartridge 122. When the closing main shaft 142 comes within a preset position range (often called a green zone), the closing limit switch 128 is triggered, and transmits information to the control unit 114.

Since tissues squeezed during closing have different thickness, when the closing limit switch 128 is triggered, but it does not absolutely mean the closing is adequate. Thus, the control unit 114 also receives the pressure value transmitted from the pressure sensor 129. When the pressure value also meets the preset standard, the control unit 114 may call a firing program, and transmits an instruction of controlling the driving motor 113 to drive the firing main shaft 1242. In this way, there is no excessive squeezing or inadequate squeezing, to ensure the tissue is squeezed adequately regardless of the thickness, and to ensure stable effect of the staple formation.

A closing switch 1123 and an opening switch 1124 connected to the control unit 114 are arranged outside the handle body 112. The closing switch 1123 is a common switch for closing and firing, so that the closing switch 1123 is required to be triggered no matter a closing action or a firing action is performed.

Only when the control unit 114 detects the closing switch 1123 is triggered, and the firing safety switch 126 is at the first operating position, the control unit 114 transmits an instruction of controlling the driving motor 113 to drive the closing main shaft 1232 to move. Thus, when the user operates the electric surgical stapler, the user needs to ensure the firing safety switch 126 is at the first operating position firstly, and then press the closing switch 1123 to start the closing action.

When the control unit 114 detects the closing switch 1123 is triggered, and the firing safety switch 126 is at the second operating position, the control unit 114 control the driving motor 113 to drive the firing main shaft 1242 to move.

The closing switch 1123 and the opening switch 1124 can be implemented by Hall switches. If a button with a magnet is arranged outside the handle body 112, the control unit 114 is provided with a Hall switch. The Hall switch may be activated by the magnet. Similarly, the Hall switch may determine whether the switching between the positions of the firing safety switch 126 is detected. The Hall switch may detect the movement of the firing safety switch 126 itself, and may detect the movement of the switching driving lever 1273.

In addition, the control unit 114 can detect whether the closing switch 1123, opening switch 1124 or the firing safety switch 126 is triggered, by the arrangement of an optoelectronic switch, a micro switch or a proximity switch.

The working head 120 also includes a firing limit switch 121A configured to detect the position of the firing main shaft 1242, and transmit information of the position to the control unit 114. When the firing limit switch 121A detects the firing main shaft 1243 comes within the preset position range, the driving motor 113 stops, and the control unit 114 transmits an instruction of prohibiting the driving motor 113 to drive the closing main shaft 1232 to move. That is, when the firing is completed, the control unit 114 may block the closing switch 1123 to disable the closing switch 1123 until a new working head is replaced. The firing limit switch 121A may be an optoelectronic switch, a micro switch or a proximity switch installed on the housing 125.

The handle 110 is removably connected to the working head 120. When the handle body 112 fits the housing 125, the handle 110 and the working head 120 are assembled together. When the housing 125 is removed from the handle body 112, the handle 110 and the working head 120 are separated from each other. The working head 120 is a circular stapling head. When the handle 110 is assembled with the working head 120, the handle 110 is a straight handle along the longitudinal direction of the working head 120, which conforms with the holding habit, to facilitate, for example, the therapy of gastrointestinal diseases.

The handle body 112 can be connected to or removed from the housing 125 rapidly. If the handle body 112 is provided with an interface part, the housing 125 is provided with a connector accordingly. During assembling, it only needs the housing 125 to be inserted into the handle body 112. The end of the output shaft 1132 is provided with an interface, and the end of the input shaft 1271 is inserted into the output shaft 1132, so the input shaft 1271 and the output shaft 1132 can assembled into a whole, while achieving the connection of the dynamical system.

A data interface 1125 connected to the control unit 114 is arranged inside the handle body 112, configured to connect the closing limit switch 128 and the pressure sensor 129. After the assembly of the handle body 112 and the housing 125, the data connector 1252 of the working head 120 is inserted into the data interface 1125.

A release button 1126 is arranged outside the handle body 112. The release button 1126 has a locking position for locking the housing and a release position for unlocking the housing. When the release button 1126 is pressed, the housing 125 is able to be inserted into the handle body 112. When the pressed release button 1126 is loosened, the housing is locked. When it is required to remove the housing 125, the release button 1126 may be pressed firstly to release locking, and then the housing may be pulled out.

The housing 125 is also provided with a window to view the motion position of the closing main shaft 1232, to facilitate the user to turn the adjustment knob manually in accordance with specific conditions. The adjustment knob 115 is able to supply a manual mode, to deal with the condition of getting stuck. In addition, when the thickness of the tissue exceeds the maximum closing ability of the device, the manual mode may be activated to make the driving motor 113 get away from the overload endless loop. In the manual mode, the anvil 121 and the cartridge 122 may be opened, or continue to finish the firing.

The electric surgical stapler further includes a replaceable battery pack 117 connected to the handle body 112, and configured to supply power to the driving motor 113. The handle body 112 is provided with an indicator light (not shown) connected to the control unit 114. The indicator light may show the closing state, the firing state or the battery level of the battery pack.

The electric surgical stapler according to the present disclosure can detect the closing pressure and the closing stroke simultaneously, to ensure the tissue is squeezed adequately regardless of the thickness of the tissue, to ensure a stable effect of the staple formation.

In the electric surgical stapler according to the present disclosure, the working head is a single-use component. The handle 110 removeably fits the working head 120. When replacing, only the working head 120 is required to be replaced, while the handle 110 can be used repeatedly after disinfection, to reduce cost. But it is necessary to point out that the above conception of detecting both the closing pressure and the closing stroke is also applicable for an integrated stapler.

The above working head 120 is a circular stapling head, but can be other types of working heads, for example, a linear stapling head.

Figure 4:
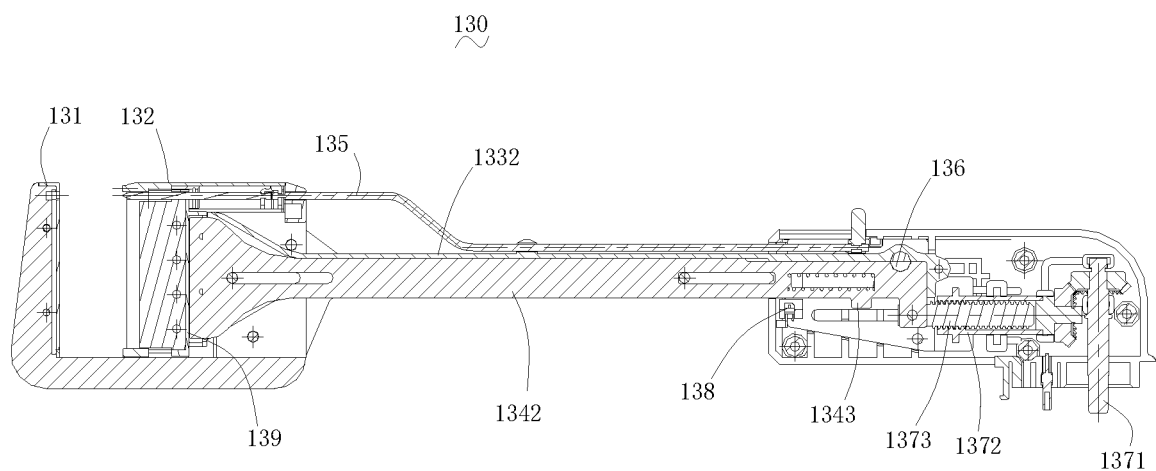
FIG. 4 is a schematic diagram illustrating a cross section of a linear stapling head.

With reference to FIG. 4, a linear working head 130 is provided, which is provided with both a closing limit switch and a pressure sensor to detect whether both the closing stroke and closing pressure meet requirements. The working head 120 can be replaced with the linear working head 130. The linear working head 130 fits the handle 110, and the mechanical connection form is the same as the above embodiment, with a difference that the device is in a shape of a gun after assembling.

With reference to FIG. 4, the linear working head 130 includes an anvil 131, a cartridge 132, a closing mechanism, a firing mechanism, and a housing 135 accommodating the closing mechanism and the firing mechanism.

The closing mechanism includes a closing lever 1332. The firing mechanism includes a firing lever 1342. The closing lever 1332 and the firing lever 1342 can move in a straight line together, or move in a straight line relative to one another.

A limit rotation shaft 136 is arranged outside the housing 135. The limit rotation shaft 136 can limit both the closing lever 1332 and the firing lever 1342 in the axial direction, to allow the closing lever 1332 and the firing lever 1342 to move together. When the limit rotation shaft 136 rotates so that the limit rotation shaft 136 is separated from the firing lever 1342 in the axial direction, the firing lever 1342 can move in a straight line relative to the closing lever 1332.

A transmission mechanism is arranged outside the housing 135, including a input shaft 1371, a thread bushing 1372 that is rotatable when driven by tapered teeth, and a screw 1373 in a threaded connection with the thread bushing 1372, and the rotation of the screw 1373 is limited so that the screw 1373 only makes axial movement. A flat fitting portion may be arranged between the screw 1373 and the thread bushing 1372, so that the screw 1373 may only translate in the axial direction. The screw 1373 is connected to the firing lever 1342 to drive the firing lever 1342 to move in a straight line. The limit rotation shaft 136 is equivalent to a firing safety switch which must be operated to switch the closing lever 1332 and the firing lever 1342.

A closing limit switch 138 is arranged inside the housing 135. At closing, the firing lever 1342 may drive the closing lever 1332 to move together, and when firing lever 1342 moves to a specified position, the raised portion 1343 on the firing lever 1342 trigger the closing limit switch 138. At firing, the limit rotation shaft 136 is operated to separate the closing lever 1332 from the firing lever 134, the firing lever 134 does not drive the closing lever 1332 when moving, and the raised portion 1343 moves and triggers the closing limit switch 138 again, to finish the firing of the cartridge.

The pressure sensor 139 is arranged on the cartridge 132. Specifically, the pressure sensor 139 may be arranged between the staple ejecting assembly of the anvil 132 and the firing lever 1342. During closing, the firing lever 1342 drives the closing lever 1332 to push the staple ejecting assembly to drive the cartridge 132 to move. Thus the pressure sensor 139 can acquire the closing pressure, can transmit the closing pressure to the control unit 114. During firing, in addition to the staple ejecting assembly, the cartridge 132 is limited in the axial direction, and the firing lever 1342 continues to push the staple ejecting assembly, so that the staple ejecting assembly moves forward relative to the cartridge 132 to finish the firing. Alternatively, the pressure sensor 139 may be arranged on the motion path of the closing lever 1332.

The linear working head 130 fits the handle 110, and is able to detect both the closing pressure and the closing stroke, to ensure the tissue is squeezed adequately regardless of the thickness, and to ensure stable effect of the staple formation.

The present invention may be carried out in other specific ways than those herein set forth without departing from the scope and essential characteristics of the invention. The present embodiments are, therefore, to be considered in all respects as illustrative and not restrictive. While embodiments and applications have been shown and described, it would be apparent to those skilled in the art having the benefit of this disclosure that many more modifications than mentioned above are possible without departing from the inventive concepts disclosed herein. The invention, therefore, is not to be restricted except in the spirit of the appended claims.

The invention claimed is:

1. An electric surgical stapler comprising:
   a handle including a handle body, a driving motor and a control unit for controlling the driving motor to operate;
   a working head including an anvil, a cartridge, a closing mechanism, a firing mechanism, a housing for accommodating the closing mechanism and the firing mechanism, a closing limit switch adapted to transmit information of a closing stroke of the closing mechanism to the control unit, and a pressure sensor configured to transmit a pressure value applied to a squeezed tissue during closing to the control unit;
   wherein the control unit is adapted to transmit an instruction of controlling the driving motor to drive the firing mechanism to move when the closing limit switch is triggered and the pressure value transmitted by the pressure sensor meets a preset standard.

2. The electric surgical stapler of claim 1, wherein the closing mechanism includes a first linear motion component adapted to drive either one of the anvil and the cartridge to move, and wherein the firing mechanism includes a second linear motion component adapted to push a staple ejecting plate in the cartridge to move.

3. The electric surgical stapler of claim 2, wherein the closing mechanism includes a closing main shaft driven by an output shaft of the driving motor to rotate, the first linear motion component is adapted to be driven by the closing main shaft and drive the anvil to move, the firing mechanism includes a firing main shaft driven by the output shaft of the driving motor to rotate, the second linear motion component is adapted to be driven by the firing main shaft and act on a staple ejecting assembly in the cartridge, and the pressure sensor is arranged on the anvil or the cartridge, or in a motion path of the first linear motion component.

4. The electric surgical stapler of claim 3, further comprising a firing safety switch having first and second operating positions, wherein the firing safety switch is adapted to allow the output shaft to transmit torque to the closing main shaft when the firing safety switch is at the first operating position, and the firing safety switch is adapted to allow the output shaft to transmit torque to the firing main shaft when the firing safety switch is at the second operating position.

5. The electric surgical stapler of claim 4, wherein a closing switch and an opening switch are coupled to the control unit and arranged outside the handle body, wherein the control unit is further adapted to transmit an instruction of controlling the driving motor to cause the closing main shaft to move when detecting that the closing switch is triggered and the firing safety switch is at the first operating position, and the control unit is further adapted to transmit an instruction of controlling the driving motor to cause the firing main shaft to move when detecting that the closing switch is triggered, the firing safety switch is at the second operating position, and the closing limit switch is in a triggered state.

6. The electric surgical stapler of claim 3, further comprising a firing limit switch adapted to detect a position of the second linear motion component and transmit position information of the second linear motion component to the control unit, wherein the control unit is further adapted to stop operation of the driving motor when the second linear motion component comes within a preset position range and triggers the firing limit switch.

7. The electric surgical stapler of claim 1, wherein the closing limit switch is selected from a group comprising an optoelectronic switch, a micro switch and a proximity switch.

8. The electric surgical stapler of claim 1, wherein a manual adjustment knob is arranged on an outer wall of the handle body, and is adapted to cause an output shaft of the driving motor to rotate when the manual adjustment knob rotates.

9. The electric surgical stapler of claim 1, wherein the housing is removably coupled to the handle body, and wherein the working head and the driving device motor are coupled together when the housing is coupled to the handle body, and the working head is separated from the driving motor when the housing is removed from the handle body.

10. The electric surgical stapler of claim 9, further comprising a data interface disposed in the handle body and coupled to the pressure sensor, the closing limit switch the firing limit switch, and the control unit.

\* \* \* \* \*